United States Patent [19]

Ratton

[11] Patent Number: 4,723,043

[45] Date of Patent: Feb. 2, 1988

[54] NITRATION OF PHENOLIC COMPOUNDS

[75] Inventor: Serge Ratton, Villefontaine, France

[73] Assignee: Rhone-Poulenc Specialites Chimiques, Courbevoie, France

[21] Appl. No.: 882,515

[22] Filed: Jul. 7, 1986

[30] Foreign Application Priority Data

Jul. 5, 1985 [FR] France .................. 85 10520

[51] Int. Cl.$^4$ .............................................. C07C 79/32
[52] U.S. Cl. .................................... 568/709; 568/779
[58] Field of Search ............... 568/709, 710, 711, 779

[56] References Cited

U.S. PATENT DOCUMENTS 3,108,927 10/1963 Pyne .................................. 568/709

FOREIGN PATENT DOCUMENTS 0070840 5/1982 Japan ................................ 568/709

*Primary Examiner*—Werren B. Lone
*Attorney, Agent, or Firm*—Burns, Doane, Swecker & Mathis

[57] ABSTRACT

Substituted phenols are nitrated by contacting same with a 10 to 70% by weight concentrated aqueous solution of nitric acid. The subject nitration process is well adopted for the preparation, e.g., of 2,6-dichloro-4-nitrophenol, a valuable intermediate in the production of various agrochemicals/pharmaceuticals.

10 Claims, No Drawings

NITRATION OF PHENOLIC COMPOUNDS

BACKGROUND OF THE INVENTION

1. Field of the Invention

The present invention relates to a process for the nitration of phenolic compounds.

2. Description of the Prior Art

It is known to this art to nitrate very many compounds, typically by using a sulfuric acid/nitric acid admixture, or also by using a dilute or concentrated solution of nitric acid. Compare, for example, "Nitration and Aromatic Reactivity" by J. G. Hoggett and R. B. Moodie (1971) published by Cambridge University Press and "Aromatic Nitration" by K. Schofield (1980) published by Cambridge University Press.

Nitrophenols (principally the ortho and para isomers) are generally prepared by nitration of phenol with nitric acid and in a sulfuric medium. See, for example, the paper by R. B. Moodie in "Journal of Chemical Society, Perkin Trans.", II, 1985, page 467.

The nitration of phenols is most frequently carried out in a sulfuric medium and rarely in an organic medium.

During the preparation of nitrophenols, certain by-products of oxidation, such as, in particular, benzoquinone derivatives and derivatives of high molecular weight originating from the condensation of several aromatic molecules, are typically observed, and this necessitates carrying out awkward purification operations.

SUMMARY OF THE INVENTION

A major object of the present invention, thus, is the provision of an improved process for the nitration of phenolic compounds, which improved process is characterized by the production, in good yields, of high purity substituted nitrophenols.

Briefly, the present invention features a process for the nitration of a phenolic compound of the formula (I):

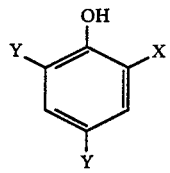

in which:

the symbol X denotes a halogen atom, a linear or branched chain alkyl radical having 1 to 4 carbon atoms or a linear or branched chain alkoxy radical having 1 to 4 carbon atoms;

one of the symbols Y denotes a hydrogen atom while the other symbol Y denotes a halogen atom, a linear or branched chain alkyl radical having 1 to 4 carbon atoms or a linear or branched chain alkoxy radical having 1 to 4 carbon atoms; comprising introducing said phenolic compound into an aqueous nitric acid solution having a concentration by weight of 10% to 70% and wherein the overall mole ratio nitric acid/phenolic compound (I) ranges from 10 to 1.2.

DETAILED DESCRIPTION OF THE PREFERRED EMBODIMENTS OF THE INVENTION

More particularly according to the present invention, the contacting of the respective reagents with each other can be carried out per any one of a number of different techniques.

Advantageously, the phenolic compound (I) can be introduced, in the solid state, into the aqueous nitric acid solution.

The nitration reaction can be accelerated by introducing into reaction medium small amounts of sodium nitrite or nitrous vapors.

The substituted nitrophenol formed, which is virtually insoluble in water, precipitates and can thereby be isolated.

Although good yields in substituted nitrophenol are thus provided, this embodiment of the process has the disadvantage of yielding a substituted nitrophenol containing the impurities which are the by-products of the reaction.

Among these impurities, benzoquinone derivatives, originating from the oxidation of the phenolic compound, occur in particular, and these discolor the substituted nitrophenol.

To lessen the effects of this problem, the phenolic compound (I) is preferably employed in the form of a solution in an apolar aprotic organic solvent which is immiscible with water.

Thus, the present invention also features a process for the nitration of a phenolic compound of the formula (I):

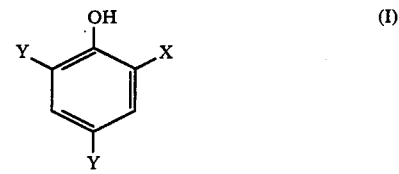

in which:

the symbol X denotes a halogen atom, a linear or branched chain alkyl group having 1 to 4 carbon atoms or a linear or branched chain alkoxy radical having 1 to 4 carbon atoms;

one of the symbols Y denotes a hydrogen atom, while the other symbol Y denotes a halogen atom, a linear or branched chain alkyl radical having 1 to 4 carbon atoms or a linear or branched chain alkoxy radical having 1 to 4 carbon atoms; comprising introducing an aqueous nitric acid solution having a concentration by weight of 10% to 70% into a solution of the phenolic compound (I) in an apolar aprotic solvent which is immiscible with water.

In the event that the reaction is carried out in this manner, it is no longer essential to have a molar excess of nitric acid relative to the phenolic compound (I). In effect, a partial conversion of the phenolic compound may suffice and, when it is desired to have complete conversion, this excess can be smaller than in the process which includes introducing the phenolic compound (I) into the aqueous nitric acid solution. In general, in the case of the aforesaid second embodiment, an overall mole ratio nitric acid/phenolic compound (I) of from 0.5 to 2 is used.

Among the phenolic compounds of the formula (I), it is more especially advantageous to employ those for which:

X denotes a bromine or chlorine atom; a methyl, ethyl, n-propyl, isopropyl, n-butyl, sec-butyl, isobutyl or tert-butyl radical; or a methoxy, ethoxy, propoxy or isopropoxy radical;

one of the symbols Y denotes a hydrogen atom, while the other symbol Y denotes a bromine or chlorine atom; a methyl, ethyl, n-propyl, isopropyl, n-butyl, sec-butyl, isobutyl, tert-butyl radical; or a methoxy, ethoxy, propoxy or isopropoxy radical.

It is especially advantageous to apply the process according to the invention to the following phenolic compounds, in particular because of the intended uses for the substituted nitrophenols which are obtained:

2,6-dichlorophenol;
2,4-dichlorophenol;
2,6-dimethoxyphenol;
2,4-dimethoxyphenol;
2,6-diethoxyphenol;
2-chloro-6-methoxyphenol;
2-chloro-4-methoxyphenol;
2,6-dimethylphenol;
2,4-dimethylphenol;
2,6-diethylphenol;
2,4-diethylphenol;
2,6-di-tert-butylphenol;
2,4-di-tert-butylphenol.

It is quite apparent that the apolar aprotic solvent used in either of the embodiments of the invention will be such as to be stable towards nitric acid under the conditions of the nitration.

Advantageously, the apolar aprotic solvent is, principally, an aliphatic hydrocarbon, a cycloaliphatic hydrocarbon, an aromatic hydrocarbon, a chlorinated aliphatic hydrocarbon, a chlorinated cycloaliphatic hydrocarbon, or a chlorinated aromatic hydrocarbon.

In order to obtain a readily isolated substituted nitrophenol of high purity, the apolar aprotic solvent is selected such that it hardly dissolves, or dissolves to only a very small extent, the said substituted nitrophenol, but, on the other hand, dissolves well the benzoquinone derivative which is formed during the reaction.

Consequently, the amount of solvent used will also be selected such as to dissolve to a sufficient extent the by-products formed and, more especially, the benzoquinone derivative.

Exemplary of the aliphatic hydrocarbons, hexane, heptane, nonane, decane and dodecane are especially representative.

Exemplary of the cycloaliphatic hydrocarbons, cyclohexane, methylcyclohexane, ethylcyclohexane, tert-butylcyclohexane, 1,1-dimethylcyclohexane, 1,2-dimethylcyclohexane, propylcyclohexane and isopropylcyclohexane are especially representative.

Exemplary of the aromatic hydrocarbons, benzene, toluene, ortho-xylene, meta-xylene, para-xylene, ethylbenzene and isopropylbenzene are especially representative.

Exemplary of the chlorinated aliphatic hydrocarbons, carbon tetrachloride, tetrachloroethylene, hexachloroethane, methylene chloride, dichloroethane, tetrachloroethane, trichloroethylene, 1-chlorobutane and 1,2-dichlorobutane are especially representative.

Exemplary of the chlorinated cycloaliphatic hydrocarbons, chlorocyclohexane is especially representative.

And exemplary of the chlorinated aromatic hydrocarbons, monochlorobenzene, 1,2-dichlorobenzene, 1,3-dichlorobenzene and 1,4-dichlorobenzene are especially representative.

Among the aforesaid groups of apolar aprotic solvents, the aromatic hydrocarbons, chlorinated aromatic hydrocarbons and chlorinated aliphatic hydrocarbons are preferably used.

Among these preferred apolar aprotic solvents, carbon tetrachloride, toluene, benzene and monochlorobenzene are the most preferred.

The initial concentration by weight of the aqueous nitric acid solution used in the present invention will preferably range from 20% to 50%.

The temperature at which the processes are carried out can vary over wide limits, for example, from 0° C. to 100° C. The reaction will preferably be performed at from 20° C. to 60° C.

The processes of the invention can be carried out discontinuously or continuously.

When the operation is carried out discontinuously, the total reaction time can be variable. In general, the time for introducing the phenolic compound varies from 15 minutes to several hours. It most frequently ranges from 30 minutes to 4 hours.

The invention enables the solvents and reagents which have not been used to be recycled easily. Thus, when an apolar aprotic solvent is used to dissolve the phenolic compound (I) and react it with the aqueous nitric acid solution, this solvent can be directly recycled after a purge, by means of which a portion of the by-products may be removed. The nitric acid solution can also be used again, after a purge, by means of which the water formed may be removed and after addition of an amount of nitric acid equal to that which has been consumed.

Among the phenolic compounds of formula (I), the processes of the invention are more especially applicable, very advantageously, to 2,6-dichlorophenol, to prepare 2,6-dichloro-4-nitrophenol. This latter compound is, in effect, an important intermediate, by means of which it is possible to obtain:

(i) by catalytic hydrogenation, for example, in the presence of a noble metal or Raney nickel, or by chemical hydrogenation, for example, using iron +hydrochloric acid, 4-amino-2,6-dichlorophenol, which is used in agrochemistry.

(ii) by methylation of the phenolic group, 2,6-dichloro-4-nitroanisole, which is an intermediate used in the pharmaceutical field.

2,6-Dichloro-4-nitrophenol is typically prepared by chlorination of 4-nitrophenol. This process is not very satisfactory, since the dichlorination is difficult to carry out and, in addition to 2,6-dichloro-4-nitrophenol, 2,5-dichloro-4-nitrophenol, 2-chloro-4-nitrophenol and 2,3,6-trichloro-4-nitrophenol are obtained, in greater or smaller amounts, and which are very difficult to separate. Moreover, 4-nitrophenol is a relatively expensive raw material.

The processes according to the invention hence provide a simple route to substituted nitrophenols of high purity an in high yields.

When the present processes are applied to 2,6-dichlorophenol, a further advantage resides in the ease of linking the nitration of the said 2,6-dichlorophenol with the synthesis of the 2,6-dichlorophenol itself, from 2-chlorophenol.

In effect, a process for selective chlorination of 2-chlorophenol to 2,6-dichlorophenol by means of gaseous chlorine includes operating at a temperature generally of from 40° C. to 120° C., in an apolar aprotic solvent and in the presence of 0.001% to 0.100% by weight, relative to the said solvent, of a primary, secondary or tertiary amine. The apolar aprotic solvent used in the chlorination of 2-chlorophenol can be, for example, carbon tetrachloride, tetrachloroethylene or monochlorobenzene, which are also very suitable for carrying out the present nitration processes.

The amine used in the chlorination of 2-chlorophenol can be, more especially, diisopropylamine, tertbutylamine or aniline.

Since this chlorination process is selective, the final solution thereby obtained of 2,6-dichlorophenol in the appropriate apolar aprotic solvent can, in practice, be used directly for the nitration by aqueous nitric acid solution, and it is thus possible to proceed very conveniently from 2-chlorophenol, which is a common industrial compound, to 2,6-dichloro-4-nitrophenol which is a very important intermediate.

The present invention is also advantageously applied to 2,6-dichlorophenol when it is mixed with other compounds, in particular with 2,4,6-trichlorophenol.

The value of a crude industrial mixture can thereby be enhanced.

It is also apparent that the processes of the invention remain very advantageous when they are applied to other phenolic compounds of formula (I), in particular to those which have been given more special attention. In order to further illustrate the present invention and the advantages thereof, the following specific examples are given, it being understood that same are intended only as illustrative and in nowise limitative.

EXAMPLE 1

A 4,000-cm$^3$ round-bottomed glass flask equipped with a thermometer, a central stirrer, a condenser and a dropping funnel was charged with 1,535 cm$^3$ of 40% strength weight/weight aqueous nitric acid solution.

The dropping funnel was charged with a solution of 2,6-dichlorophenol in carbon tetrachloride (200 g of 2,6-dichlorophenol dissolved in 1,230 cm$^3$ of carbon tetrachloride).

The nitric acid solution was heated to 35° C. by means of a water bath; the 2,6-dichlorophenol solution was then introduced therein, over 1 hr, 30 min.

During the addition, a separation between the aqueous nitric acid layer and the carbon tetrachloride, the appearance of a precipitate and a slight evolution of reddish-brown vapors were observed in the reaction mass.

When the addition was complete, stirring was continued for 5 minutes.

The mixture was then cooled to approximately 4° C. by means of ice. The precipitate was drained on a sintered glass filter, washed twice with 100 cm$^3$ of ice-cold water and then dried under vacuum in a desiccator.

229 g of pure 2,6-dichloro-4-nitrophenol (without by-products and, in particular, without 2,6-dichlorobenzoquinone) containing 1.3% of water were thereby recovered.

Yield of product isolated, relative to the 2,6-dichlorophenol charged (RY): 87%.

The 2,6-dichloro-4-nitrophenol was a pale yellow powder.

The organic phase and the aqueous phase were separated by decantation; in each phase, the dissolved 2,6-dichloro-4-nitrophenol and the 2,6-dichlorobenzoquinone were assayed by high performance liquid chromatography.

Total RY of 2,6-dichloro-4-nitrophenol: 90.2% (the 2,6-dichloro-4-nitrophenol isolated did not contain 2,6-dichlorobenzoquinone).

RY of 2,6-dichlorobenzoquinone: 8.9%.

It was noted that the 2,6-dichlorobenzoquinone predominated in the organic phase.

EXAMPLE 2

A 250-cm$^3$ round-bottomed glass flask equipped with a thermometer, a central stirrer, a condenser and a dropping funnel was charged with 60 cm$^3$ of 25% strength weight/weight aqueous nitric acid solution. The dropping funnel was charged with a solution of 2,6-dichlorophenol in carbon tetrachloride (8.15 g of 2,6-dichlorophenol dissolved in 50 cm$^3$ of carbon tetrachloride).

The nitric acid solution was heated to 35° C. by means of a water bath; the 2,6-dichlorophenol solution was then introduced therein, over 30 minutes.

During the addition, a separation between the aqueous nitric acid layer and the carbon tetrachloride, the appearance of a precipitate and a slight evolution of reddish-brown vapors were observed in the reaction mass.

When the addition was complete, stirring was continued for 5 minutes.

The mixture was then cooled to approximately 4° C. by means of ice. The precipitate was drained on a sintered glass filter, washed twice with 10 cm$^3$ of ice-cold water and then dried under vacuum in a desiccator.

Weight of product isolated: 8.80 g (including 8.70 g of pure 2,6-dichloro-4-nitrophenol).

The product isolated did not contain 2,6-dichlorobenzoquinone.

The organic phase and the aqueous phase was separated by decantation; in each phase, the dissolved 2,6-dichloro-4-nitrophenol and 2,6-dichlorobenzoquinone were assayed by high performance liquid chromatography.

Total RY of 2,6-dichloro-4-nitrophenol: 86.1%.

EXAMPLE 3

Example 2 was repeated, charging 60 cm$^3$ of 35% strength weight/weight aqueous nitric acid solution. The procedure, the amount of 2,6-dichlorophenol, the solvent and the reaction time were the same as in Example 2.

Weight of the product isolated: 8.75 g (including 8.67 g of pure 2,6-dichloro-4-nitrophenol).

The product isolated did not contain 2,6-dichlorobenzoquinone.

Total RY of 2,6-dichloro-4-nitrophenol: 86.8%.

RY of 2,6-dichlorobenzoquinone: 8.0%.

EXAMPLE 4

Example 2 was repeated, charging 60 cm$^3$ of 45% strength weight/weight aqueous nitric acid solution. The procedure, the amount of 2,6-dichlorophenol, the solvent and the reaction time were the same as in Example 2.

Weight of the product isolated: 9.0 g (including 8.82 g of pure 2,6-dichloro-4-nitrophenol).

The product isolated did not contain 2,6-dichlorobenzoquinone.
Total RY of 2,6-dichloro-4-nitrophenol: 88.8%.
RY of 2,6-dichlorobenzoquinone: 6.8%.

EXAMPLE 5

Example 2 was repeated, charging 60 cm$^3$ of 60% strength weight/weight aqueous nitric acid solution. The procedure, the amount of 2,6-dichlorophenol, the solvent and the reaction time were the same as in Example 2.

Weight of the product isolated: 7.50 g (including 7.35 g of pure 2,6-dichloro-4-nitrophenol).

The product isolated did not contain 2,6-dichlorobenzoquinone.
Total RY of 2,6-dichloro-4-nitrophenol: 74.4%.
RY of 2,6-dichlorobenzoquinone: 9.5%.

EXAMPLE 6

Example 2 was repeated according to the same procedure and the same reaction times, but with the following amounts of reagents and solvent:
35% strength weight/weight aqueous nitric acid solution: 60 cm$^3$
solution of 8.15 g of 2,6-dichlorophenol in 50 cm$^3$ of toluene.

Weight of the product isolated: 7.95 g (including 7.78 g of pure 2,6-dichloro-4-nitrophenol).

The product isolated did not contain 2,6-dichlorobenzoquinone.
Total RY of 2,6-dichloro-4-nitrophenol: 88.9%.
RY of 2,6-dichlorobenzoquinone: 10.6%.

EXAMPLE 7

Example 2 was repeated according to the same procedure and the same reaction times, but with the following amounts of reagents and solvent:
35% strength weight/weight aqueous nitric acid solution: 60 cm$^3$
solution of 8.15 g of 2,6-dichlorophenol in 50 cm$^3$ of monochlorobenzene.

Weight of the product isolated: 7.65 g (including 7.21 g of pure 2,6-dichloro-4-nitrophenol).

The product isolated did not contain 2,6-dichlorobenzoquinone.
Total RY of 2,6-dichloro-4-nitrophenol: 86.8%.
RY of 2,6-dichlorobenzoquinone: 11.3%.

EXAMPLE 8

Example 2 was repeated according to the same procedure and the same reaction times, but with the following amounts of reagents and solvent:
35% strength weight/weight aqueous nitric acid solution: 60 cm$^3$
solution of 8.15 g of 2,6-dichlorophenol in 50 cm$^3$ of cyclohexane.

Weight of the product isolated: 9.73 g (including 9.10 g of pure 2,6-dichloro-4-nitrophenol and 90.39 g of 2,6-dichlorobenzoquinone).
Total RY of 2,6-dichloro-4-nitrophenol: 89.0%.
RY of 2,6-dichlorobenzoquinone: 11.4%.

EXAMPLE 9

Example 2 was repeated according to the same procedure and the same reaction times, but with the following amounts of reagents and solvent:
45% strength weight/weight aqueous nitric acid solution: 14 g
solution of 8.15 g of 2,6-dichlorophenol in 25 cm$^3$ of carbon tetrachloride (saturated solution).

Weight of the product isolated: 9.62 g (including 9.13 g of pure 2,6-dichloro-4-nitrophenol and 0.12 g of 2,6-dichlorobenzoquinone).
Total RY of 2,6-dichloro-4-nitrophenol: 89.4%.
RY of 2,6-dichlorobenzoquinone: 12.2%.

EXAMPLE 10

A 125-cm$^3$ round-bottomed glass flask equipped with a thermometer, a central stirrer and a condenser was charged with 25 cm$^3$ of 40% strength weight/weight aqueous nitric acid solution, which was brought to 35° C.

3.26 g of 2,6-dichlorophenol were introduced over the course of approximately 15 minutes using a spatula. No immediate reaction was observed. A few crystals of sodium nitrite were added in order to catalyze the reaction. A yellow coloring of the reaction mass was noted.

The reaction was slow; the mixture was maintained overnight under stirring at 35° C.

The reaction mass then contained a yellow precipitate. The precipitate was drained, washed twice with 5 cm$^3$ of ice-cold water and dried under vacuum in a desiccator.

RY of 2,6-dichloro-4-nitrophenol: 79.0%.

EXAMPLE 11

The apparatus described in Example 2 was charged with:
20 g (122.7 mmol) of 2,6-dichlorophenol,
130 cm$^3$ of carbon tetrachloride.

The mixture was heated to 35° C. 29 g of 40% strength (by weight) aqueous nitric acid solution (184 mmol) were then introduced therein, over 20 minutes.

During the addition, the reaction mass rapidly assumed a yellow color; a yellow precipitate, a slight separation and an evolution of reddish-brown vapors were then noted.

When the addition was complete, the mixture was maintained under stirring for 15 minutes at the temperature and then cooled to 0° C. The mixture was filtered and the precipitate washed with water, drained and dried.

Weight of the 2,6-dichloro-4-nitrophenol isolated: 22.64 g.

The product isolated did not contain 2,6-dichlorobenzoquinone.

The organic phase and the aqueous phase were separated by decantation; in each phase, the dissolved 2,6-dichloro-4-nitrophenol and the 2,6-dichlorobenzoquinone were assayed by high performance liquid chromatography.

The following results were obtained:
Degree of conversion (DC) of 2,6-dichlorophenol: 100%.
RY of 2,6-dichloro-4-nitrophenol isolated: 88.7%.
RY of total 2,6-dichloro-4-nitrophenol: 91.4%.
RY of 2,6-dichlorobenzoquinone: 8.2%.

EXAMPLE 12

Nitration of a mixture of 2,6-dichlorophenol and 2,4,6-trichlorophenol

An apparatus similar to that of Example 2, but with a 500-cm$^3$ reactor, was charged with:
36.8 g (225.76 mmol) of 2,6-dichlorophenol,
3.68 g (18.64 mmol) of 2,4,6-trichlorophenol, 360 g of carbon tetrachloride.

A solution was obtained which was approximately 10% by weight in carbon tetrachloride. The mixture was heated to 35° under stirring.

53.55 g of a 40% strength (by weight) nitric acid solution were introduced therein, over 15 minutes (338 mmol: 1.5 times the molar amount of 2,6-dichlorophenol).

During the addition, the reaction mass rapidly assumed a yellow color; a yellow precipitate, a slight separation and an evolution of reddish-brown vapors were then noted.

When the addition was complete, the mixture was orange; it was maintained under stirring for 15 minutes at the temperature and then cooled to 0° C. The mixture was filtered and the precipitate washed with water, drained and dried.

Weight of the 2,6-dichloro-4-nitrophenol isolated: 41.70 g.

The product isolated did not contain 2,6-dichlorobenzoquinone.

The organic phase and the aqueous phase were separated by decantation; in each phase, the dissolved 2,6-dichloro-4-nitrophenol and the unreacted 2,4,6-trichlorophenol were assayed by high performance liquid chromatography.

The following results were obtained:
DC of the 2,6-dichlorophenol: 100%
RY of 2,6-dichloro-4-nitrophenol isolated: 88.8%
RY of total 2,6-dichloro-4-nitrophenol: 91.5%.
2.1 g of unreacted 2,4,6-trichlorophenol were found.

EXAMPLE 13

Nitration of a mixture of 2,6-dichlorophenol and 2,4,6-trichlorophenol:

An apparatus similar to that of Example 2, but with a 6-1 reactor, was charged with 1,293 g (8.4 mol) of 40.9% strength (by weight) aqueous nitric acid solution.

The mixture was heated to 33° C. under stirring. A piston pump was used to inject, over the course of 2 hr, 50 min, 3,600 g (2,280 cm$^3$) of a solution of 2,6-dichlorophenol and 2,4,6-trichlorophenol in carbon tetrachloride containing:

2.098 mols of 2,6-dichlorophenol (9.5% by weight in the solution),
0.169 mols of 2,4,6-trichlorophenol (0.93% by weight in the solution).

An evolution of nitrous vapors was noted throughout the period of the injection.

When the injection was complete, the mixture was cooled to 4° C. by means of ice, over 55 minutes.

The mixture was filtered on a Büchner filter; the precipitate was washed with 700 cm$^3$ of water; it was drained and dried.

366 g of 2,6-dichloro-4-nitrophenol were obtained (no 2,6-dichlorobenzoquinone).

The organic phase and the aqueous phase were separated by decantation; in each phase, the dissolved 2,6-dichloro-4-nitrophenol and the 2,6-dichlorobenzoquinone were assayed by high performance liquid chromatography.

The following results were obtained:
DC of the 2,6-dichlorophenol: 100%
RY of 2,6-dichloro-4-nitrophenol isolated: 84.0%
RY of total 2,6-dichloro-4-nitrophenol: 87.3%.
RY of 2,6-dichlorobenzoquinone: 9.4%.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the nitration of 2,6-dichlorophenol comprising introducing said 2,6-dichlorophenol in solution in an apolar aprotic solvent, said solvent being immiscible in water, into a 20 to 50% by weight concentrated aqueous solution of nitric acid, with the molar ratio nitric acid/2,6-dichlorophenol ranging from 10 to 1.2.

2. A process for the nitration of 2,6-dichlorophenol comprising introducing a 10 to 70% by weight concentrated aqueous solution of nitric acid into a solution of said 2,6-dichlorophenol in an apolar aprotic solvent, said solvent being immiscible with water.

3. The process as defined by claims 1 or 2, said apolar aprotic solvent comprising an aliphatic hydrocarbon, a cycloaliphatic hydrocarbon, an aromatic hydrocarbon, a chlorinated aliphatic hydrocarbon, a chlorinated cycloaliphatic hydrocarbon, or a chlorinated aromatic hydrocarbon.

4. The process as defined by claim 3, said apolar aprotic solvent comprising an aromatic hydrocarbon, chlorinated aromatic hydrocarbon or chlorinated aliphatic hydrocarbon.

5. The process as defined by claim 4, said apolar aprotic solvent comprising carbon tetrachloride, toluene, benzene or monochlorobenzene.

6. The process as defined by claims 1 or 2, said nitration being carried out at a temperature of from 0° C. to 100° C.

7. The process as defined by claims 1 or 2, said 2,6-dichlorophenol prepared by selective chlorination of 2-chlorophenol with gaseous chlorine in an apolar aprotic solvent and in the presence of 0.001% to 0.100% by weight, relative to said solvent, of a primary, secondary or tertiary amine.

8. The process as defined by claims 1 or 2, said nitration reaction medium comprising a minor amount of sodium nitrite or nitrous vapors.

9. The process as defined by claim 2, wherein the molar ratio nitric acid/2,6-dichlorophenol ranges from 0.5 to 2.

10. The process as defined by claims 1 or 2, wherein said nitration includes nitrating an admixture of said 2,6-dichlorophenol and 2,4,6-trichlorophenol.

* * * * *